United States Patent [19]
Rankin et al.

[11] Patent Number: 5,476,456
[45] Date of Patent: Dec. 19, 1995

[54] DISPOSABLE ABSORBENT COVER FOR PATIENT SUPPORTING ARTICLE

[76] Inventors: Paul Rankin, 1536 Conneaut Ave., Bowling Green, Ohio 43402; Jack R. VonEwegen, 341 Sycamore La., Perrysburg, Ohio 43551

[21] Appl. No.: 251,719

[22] Filed: May 27, 1994

[51] Int. Cl.[6] .............................. A61F 13/15; A61F 13/20
[52] U.S. Cl. .................... 604/358; 604/368; 604/372; 604/385.1; 128/849
[58] Field of Search ..................... 604/358, 367, 604/368, 369, 372, 385.1; 128/849, 852, 854, 855, 856

[56] References Cited

U.S. PATENT DOCUMENTS

| | | | |
|---|---|---|---|
| 3,731,689 | 5/1973 | Schaar | 604/369 |
| 3,799,167 | 3/1974 | Miller et al. | 604/372 |
| 3,986,505 | 10/1976 | Power. | |
| 4,015,604 | 4/1977 | Csillag | 604/365 |
| 4,212,302 | 7/1980 | Karami | 604/368 |
| 4,813,944 | 3/1989 | Haney et al. | |
| 4,943,286 | 7/1990 | Armstead. | |
| 5,061,235 | 10/1991 | Hogan. | |
| 5,255,303 | 10/1993 | DiMaio et al. | |
| 5,290,268 | 3/1994 | Oliver et al. | 604/360 |

FOREIGN PATENT DOCUMENTS

| | | | |
|---|---|---|---|
| 2399824 | 4/1979 | France | 604/358 |
| 2269579 | 2/1994 | United Kingdom | 128/899 |

*Primary Examiner*—Randall L. Green
*Assistant Examiner*—P. Zuttarelli
*Attorney, Agent, or Firm*—Gifford, Krass, Groh, Sprinkle, Patmore, Anderson & Citkowski

[57] ABSTRACT

A disposable cover for a patient support surface which allows absorption of body fluids from the patient and prevents contamination of the support surface. The ends of the cover are provided with pockets to contain the cover in a rolled up condition prior to use and after-use for disposal. The pockets are reverse folded to contain the ends of the support surface when the pad is in its use position.

12 Claims, 2 Drawing Sheets

DISPOSABLE ABSORBENT COVER FOR PATIENT SUPPORTING ARTICLE

BACKGROUND OF THE INVENTION

1. Field of the Invention

This invention relates to a disposable cover for a patient support surface, and, more particularly, this invention relates to a liquid absorbent and liquid barrier cover to prevent contaminating body fluid and administered fluid exchange between the support structure and the patient.

2. State of the Prior Art

There are a wide variety of covers and pads used in combination with patient supports such as stretchers or gurneys for confining contamination from potentially hazardous body fluids and fluids being administered such as intervenous solutions during treatment and emergency transport. Many of these covers or pads employ a liquid pervious outer bottom layer, an absorbent inner layer, and another absorbent or a liquid pervious outer top layer. These pads or covers are usually of the permanent or reusable type, and particularly where they are not attached to the patient support structure, they often have their edges joined as by stitching or sealed by a glue or heat bond. Typically, the unattached cover or pad is used in a hospital or emergency facility operating in an environment to absorb blood during an operation or as an underpad in a hospital or nursing home for incontinent patients. When the cover is attached to an underlying support surface, it is typically attached by a glue or attachment straps.

Even where the cover is manufactured to be disposable, the prior art articles do not provide a means for ready attachment to the use surface nor the means for packaging or preparing the device for ready use or for disposal of the used cover while containing contamination.

SUMMARY OF THE INVENTION

The present invention provides a disposable cover for a patient support surface. The cover absorbs fluids such as body fluids and fluids being administered to the patient and prevents exchange of these fluids between the patient and the support surface.

The cover has a stretchable fluid impervious plastic bottom sheet and a layer of absorbent material. Preferably the cover also has a top sheet of liquid pervious material such as a polypropylene or polyester nonwoven plastic fiber material. The top sheet provides a more comfortable skin contact surface and acts to confine any dusting that may occur in the absorbent material layer.

In the present invention the bottom sheet is selected with an appropriate elasticity or stretchability and the sheet is provided with pockets at each end of the sheet that extend across the width of the cover so that the cover can be rolled up and inserted into one of the end pockets for before-use handling and after-use disposal In use, the cover is unrolled and the pockets at each end are folded inside out so that the ends of a patient support surface or a pad or mattress on such a surface can be inserted into the pockets as the bottom sheet elastically yields. After use, the contaminated cover with its absorbed liquid can be handled in a safe manner by inserting a hand into the pockets as the cover is removed from the pad and as one of the pockets is again turned inside out to its original position to receive the rolled up used cover. Thus the new cover and its method of use provides a very significant advancement over the prior art.

Another aspect of the invention is the use of a super absorbent polymer in the absorbent material to increase absorptivity in a conventional manner. In a preferred embodiment, the super absorbent polymer is added in a selected manner along marginal strips on each side of the width of the bottom sheet so that as water is absorbed, gel dams will be created at each side of the sheet to contain most of the collected fluids, leaving the central portion of the absorbent pad in contact with the patient relatively dry. This eliminates the "slimy" condition that can occur when the superabsorbent is dispersed throughout the layer.

BRIEF DESCRIPTION OF THE DRAWING

The preferred embodiment of the invention is illustrated in the drawing in which.

DESCRIPTION OF THE PREFERRED EMBODIMENTS

Figure 5:
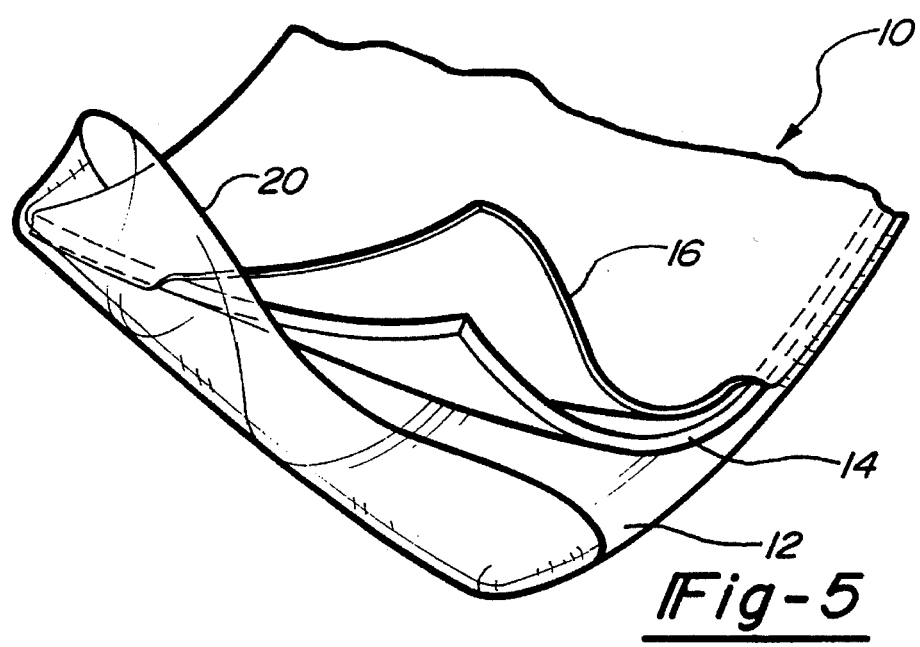
FIG. 5 is an exploded perspective view of an end portion of the cover showing the laminated construction of the cover and the end pocket formed in the bottom sheet of the cover.

As best seen in FIG. 5, the disposable cover 10 of the invention includes a stretchable fluid impervious plastic bottom sheet 12, an intermediate layer of absorbent material 14 and a top sheet 16 of liquid pervious material covering the absorbent layer. The layers preferably are laminated together by gluing or heat sealing.

The bottom sheet provides a moisture impervious barrier which prevents liquid flow and consequent patient and environment contamination. The bottom sheet is made of a stretchable or pliable plastic film of the order of 0.002" thick. Proper stretchability is provided, for example, in a polyurethane material. The bottom sheet will have a length and width to hold or circumscribe the patient, with these dimensions also allowing it to be fit over the patient support surface such as a stretcher pad.

The intermediate layer 14 of absorbent material is a cellulose packing such as bleached wood pulp as is typically used in disposable baby diapers and other sanitary products. Preferably the unwoven fibers are formed into a mat by a fluff mat forming process and will typically be of between 3/16" to 1/4" thick.

Preferably the absorbent material is selectively impregnated with a superabsorbent polymer to increase overall absorption.

Figure 2:
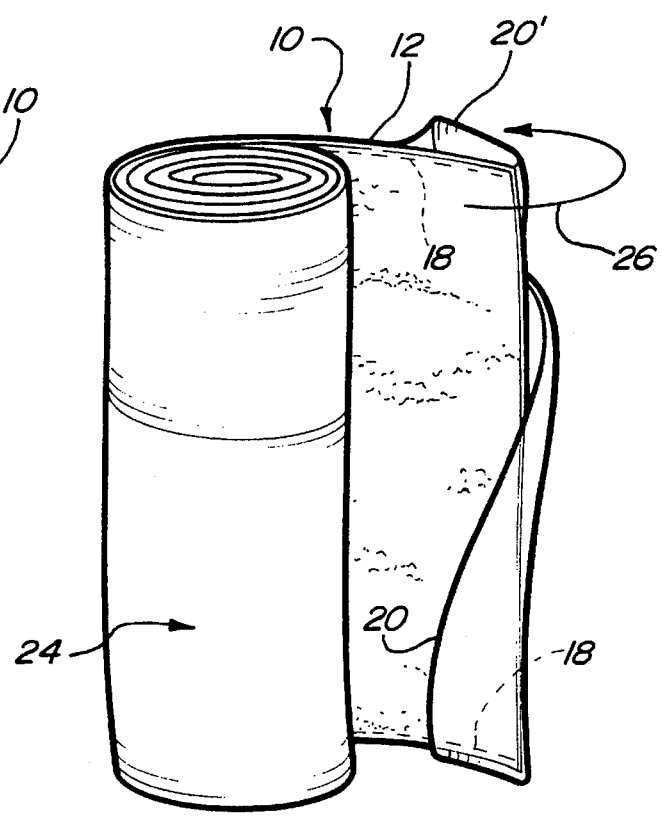
FIG. 2 is a perspective view similar to FIG. 1 showing the disposable cover disengaged from its storage end pocket and partially unrolled showing the manner in which the end pocket can be folded inside out to prepare it for its use condition.
Figure 3:
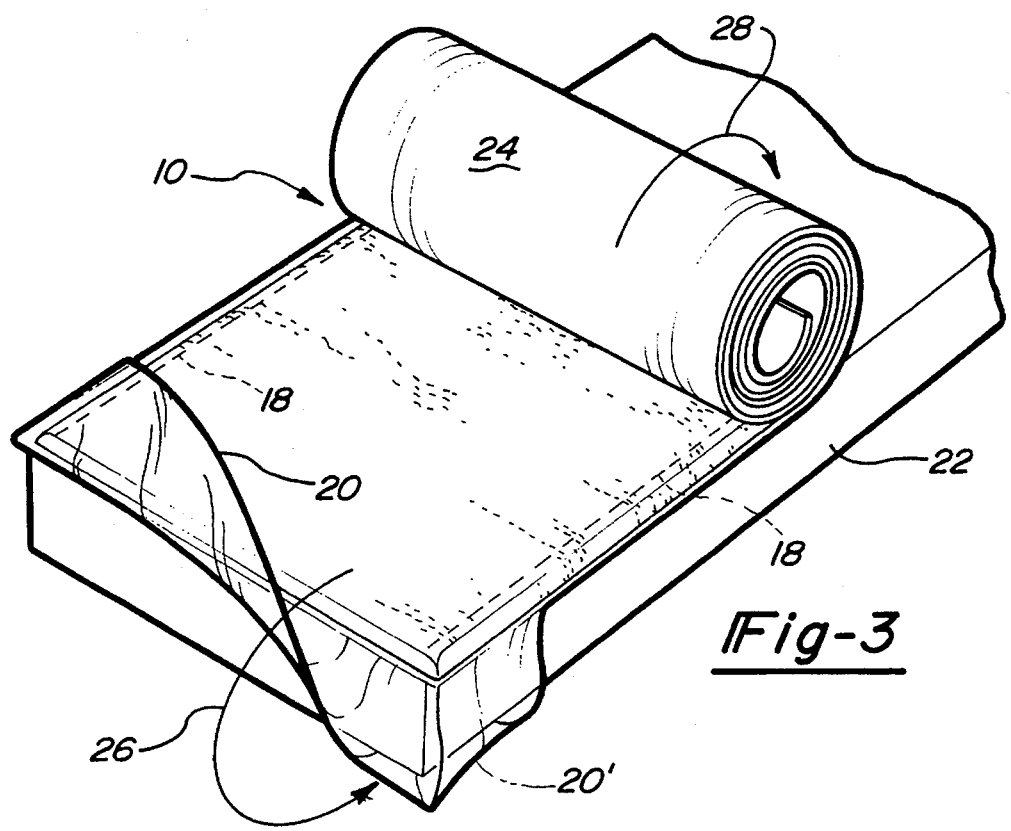
FIG. 3 is a perspective view with the cover placed over a pad or mattress of a patient transport or treatment device with the pocket at one end of the cover being turned inside out to form a pocket for engaging one end of the pad or mattress.

In a preferred embodiment of the invention, the superabsorbent is applied as a marginal strip 18 along each edge of the absorbent layer as shown best in FIGS. 2 and 3. This allows a gel dam to form confining the moisture and concentrating it in this marginal area to avoid over saturation and a consequent slimy condition that can be produced when the superabsorbent is dispersed throughout the absorbent layer.

A top layer 16 is a water pervious layer to allow the fluid to pass through it into the absorbent layer. Preferably the material of the top layer is a nonwoven polyprolyene or a polyester plastic. The top layer acts as a buffer which is more comfortable to the touch than the absorbent layer and it acts to confine any particles of the absorbent layer which may break away from the core.

A pocket 20 is formed at each end of the bottom layer 12, extending upward in the direction of the laminated intermediate absorbent layer 14 and top layer 16 as shown in FIG. 5.

Figure 1:
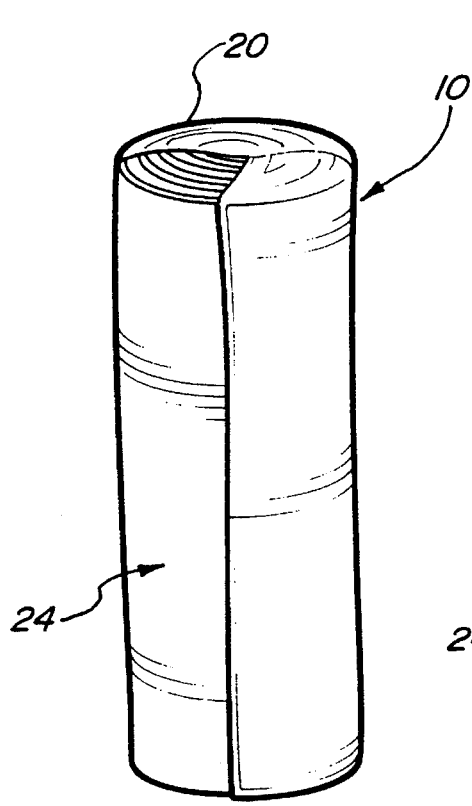
FIG. 1 is a perspective view of the disposable absorbent cover according to the invention shown in its rolled-up storage position with the roll inserted into a pocket at one end of the cover as it would be in its before-use condition for handling and storage or in its after-use contaminated condition for disposal.
Figure 4:
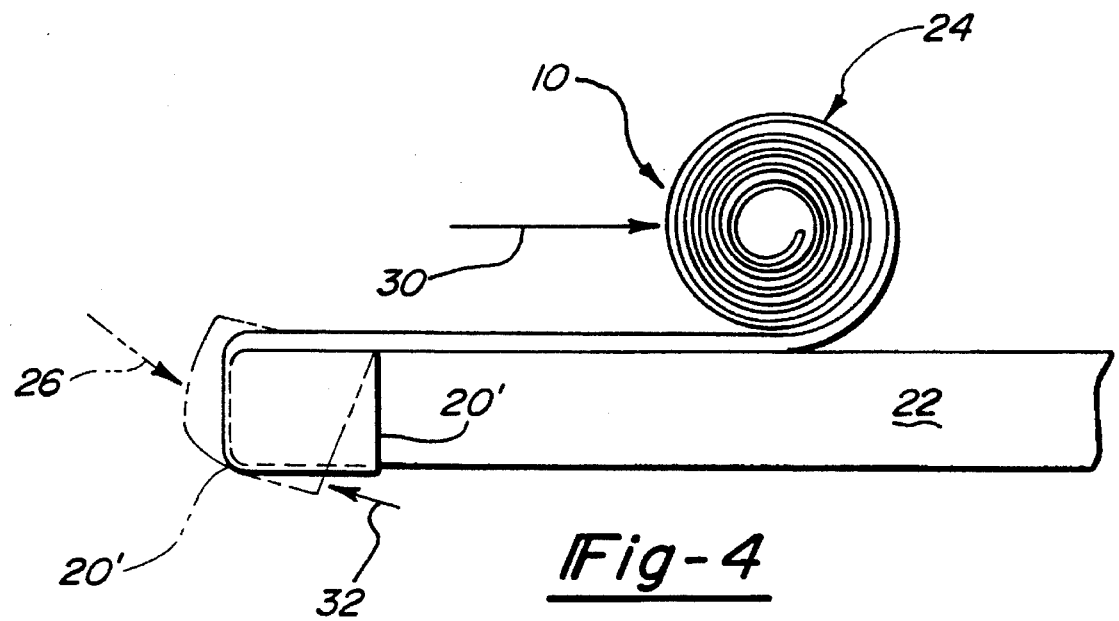
FIG. 4 is a side elevational view of the cover of the invention as shown in FIG. 3 with one end of the patient transport and treatment device pad inserted into the end pocket of the cover.

The cover 10 is prepared and packaged for ready use by rolling the cover up upon itself into a roll 24 and inserting it into one of the end pockets 20 as shown in FIG. 1. When the cover is to be used on a work support surface such as a stretcher pad or mattress 22 as shown in FIGS. 3 and 4 the roll 24 is slipped out of the pocket 20 and partially unrolled as shown in FIG. 2. The pocket 20 can then be folded inside out as shown by the arrow 26 so that it extends outwardly from the unlaminated side of bottom sheet 12 as shown at 20'. One end of the pad 22 can then be slipped into the pocket 20' as shown in FIGS. 3 and 4. The roll 24 can then be further unrolled as shown by arrows 28 and 30 in FIGS. 3 and 4. The pocket 20 at the other end of the roll can then be turned inside out so that the other end of the stretcher pad 22 can be inserted within the pocket.

After the use has been completed, the cover can be removed safely by hand insertion into the pocket 20' as shown by arrow 32 in FIG. 4 to assist in removing the end of the pad 22 from the cover, and for again turning the pocket 20' inside out to its original position 20 to again receive the roll 24 in the manner shown in the original packaging of FIG. 1 for disposal.

Having described my invention however many modifications thereto will become apparent to those skilled in the art to which it pertains without deviation from the spirit of the invention as defined by the scope of the appended claims.

We claim:

1. A disposable cover for a patient support surface such as a stretcher pad and the like for preventing contaminating body fluid and administered fluid exchange between the pad and patient, comprising:

a stretchable fluid impervious plastic bottom sheet having a length and width to fit over said pad and to circumscribe the patient;

a layer of absorbent material on said bottom sheet;

said bottom sheet having pockets extending across the width of said bottom sheet at opposed ends of said sheet and said pockets extending toward said layer of absorbent material;

whereby the cover can be rolled up to be inserted into and to be retained by one of said pockets in its before-use condition for storage and in its after-use contaminated condition for contained disposal, and said cover can be retained on said patient support surface by folding said pockets inside out over said bottom sheet to receive opposed ends of said pad.

2. The disposable cover according to claim 1 wherein said pockets have been formed by folding over said bottom sheet at both opposed ends, forming flaps, and sealing said flaps at opposed sides along the length of said bottom sheet.

3. The disposable cover according to claim 1 wherein said layer of absorbent material is a preformed mat of cellular packing.

4. The disposable cover according to claim 3 wherein said absorbent material is a bleached wood pulp.

5. The disposable cover according to claim 3 wherein a super absorbent polymer is selectively dispersed throughout said mat.

6. The disposable cover according to claim 1 further including a top sheet of pervious material covering said layer of absorbent material.

7. The disposable cover according to claim 6 wherein said top sheet is an unwoven material.

8. The disposable cover according to claim 7 wherein said bottom sheet, said layer of absorbent material and said top sheet are bonded together.

9. The disposable cover according to claim 6 wherein a super absorbent polymer is applied to a marginal strip on each side of the width of said absorbent material to create gel dams as liquid is absorbed in said absorbent material.

10. A method of protecting a patient during transport and treatment from contamination from a pad, mattress or the like on a transport or treatment device such as a stretcher and for preventing contamination of the pad on the device by the patient's body fluids or fluids being administered to the patient, comprising the following steps:

A) forming a laminated cover including a stretchable fluid impervious bottom sheet having a length and width to fit over said pad and circumscribe the patient, an intermediate layer of absorbent material and a top sheet of liquid pervious material;

B) forming pockets in the bottom sheet extending across the width of the sheet at opposed ends and extending from the laminated side of the sheet;

C) rolling the cover up and inserting the roll into the pocket at one end of the sheet for before-use handling and storage;

D) removing the roll from its pocket and partially unrolling the cover;

E) turning the pocket inside out so that the pocket extends away from the unlaminated side of the bottom sheet;

F) inserting one end of the transport device pad into the pocket formed in step E;

G) completing the unrolling of the cover over the transport pad and folding the exposed pocket at the other end of the cover inside out so that the pocket extends away from the unlaminated side of the bottom sheet;

H) inserting the other end of the transport device pad into the pocket formed in step G;

I) using the transport device with a patient laying on the cover;

J) removing both ends of the transport device pad from the pockets in which they are contained;

K) reverse inside out folding at least one of the pockets so that it extends outwardly from the laminated side of the cover;

L) rolling the cover up towards the at least one reverse folded pocket and inserting the roll into the pocket.

11. The method according to claim 10 in which the steps of the method are sequentially performed.

12. The method according to claim 10 including the step of using at least one of the pockets folded inside out in steps E and G for protected hand insertion during roll-up of the cover in step L.

* * * * *